United States Patent
Aoi et al.

(10) Patent No.: US 7,881,431 B2
(45) Date of Patent: Feb. 1, 2011

(54) RADIOTHERAPY APPARATUS AND RADIATION IRRADIATING METHOD

(75) Inventors: Tatsufumi Aoi, Hiroshima-ken (JP);
Ichiro Yamashita, Hiroshima-ken (JP);
Kazuhiro Tsukuda, Hiroshima-ken (JP);
Etsuro Hirai, Hiroshima-ken (JP);
Yuichiro Kamino, Aichi-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 12/366,385

(22) Filed: Feb. 5, 2009

(65) Prior Publication Data
US 2010/0034352 A1    Feb. 11, 2010

(30) Foreign Application Priority Data
Aug. 6, 2008    (JP) ............................ 2008-203155

(51) Int. Cl.
*A61N 5/10* (2006.01)
(52) U.S. Cl. ......................................... 378/65; 378/108
(58) Field of Classification Search .................. 378/65, 378/108, 109, 110
See application file for complete search history.

(56) References Cited

U.S. PATENT DOCUMENTS

| | | | |
|---|---|---|---|
| 4,427,890 A | 1/1984 | Taumann | |
| 2004/0247080 A1* | 12/2004 | Feda | ......................... 378/101 |
| 2005/0100133 A1 | 5/2005 | Reinhold | |
| 2007/0248214 A1* | 10/2007 | Smith | ......................... 378/109 |

FOREIGN PATENT DOCUMENTS

| | | |
|---|---|---|
| EP | 1530408 A2 | 5/2005 |
| JP | 6-84664 U | 12/1994 |
| JP | 2004-321408 A | 11/2004 |
| JP | 2005-340009 A | 12/2005 |
| JP | 2008-27360 A | 2/2008 |
| WO | WO 03/101298 A2 | 12/2003 |

OTHER PUBLICATIONS

Medduagh, G. E. "The R.F. System of a Typical Clinical Linear Accelerator", IEEE MTT-S Digest, TH3D-2, IEEE MTT-S International, May 23, 1994, XP010586494, pp. 1611-1614.

* cited by examiner

*Primary Examiner*—Chih-Cheng G Kao
(74) *Attorney, Agent, or Firm*—Birch, Stewart, Kolasch & Birch, LLP

(57) ABSTRACT

A radiotherapy apparatus includes an acceleration unit configured to generate a charged particle beam. A target is configured to generate a radiation when the charged particle beam is irradiated to the target. A sensor is configured to measure an electric current flowing through the target. A dosimeter is configured to measure a dose of the radiation. A control unit is configured to control the acceleration unit based on the measured electric current and the measured dose.

17 Claims, 5 Drawing Sheets

RADIOTHERAPY APPARATUS AND RADIATION IRRADIATING METHOD

INCORPORATION BY REFERENCE

This patent Application claims priority on convention based on Japanese Patent Application No. 2008-203155. The disclosure thereof is incorporated herein by reference.

BACKGROUND OF THE INVENTION

1. Field of the Invention

The present invention relates to a radiotherapy apparatus and a radiation irradiating method, and especially relates to a radiotherapy apparatus and a radiation irradiating method in which a high stability of doses can be realized in radiotherapy for, for example, a prostate and a lung as an affected region of tumor in a body's interior.

2. Description of Related Art

A radiotherapy apparatus for treating a patient by irradiating a therapeutic radiation to an affected region (a tumor) is widely known. The radiotherapy is required to have a high therapeutic effect. Additionally, it is required to irradiate only a predetermined dose of the therapeutic radiation to the affected region more accurately, and fluctuation of the dose is required to be small.

U.S. Pat. No. 4,427,890 discloses a method for controlling energy of an electron beam by monitoring an electric current in a target which converts an electron beam into the X-ray. US Patent Application Publication No. 2007/0248214 discloses a method for controlling energy of an electron beam by measuring a dose distribution of the X-ray with using a transmission type dosimeter having a dispersion type terminal electrode and by controlling power so as to correct a change of the dose distribution of the X-ray.

SUMMARY

The present invention provides a radiotherapy apparatus and a radiation irradiating method, in which fluctuation of a dose of a radiation irradiated to a sample can be reduced.

In an aspect of the present invention, a radiotherapy apparatus includes: an acceleration unit configured to generate a charged particle beam. A target is configured to generate a radiation when the charged particle beam is irradiated to the target. A sensor is configured to measure an electric current flowing through the target. A dosimeter is configured to measure a dose of the radiation. A control unit is configured to control the acceleration unit based on the measured electric current and the measured dose.

In another aspect of the present invention, a radiation irradiating method is achieved by measuring electric current flowing through a target which irradiates radiation when a charged particle beam generated by an acceleration unit is irradiated; by measuring a dose of the radiation; and by controlling the acceleration unit based on the measured electric current and the measured dose.

In a radiotherapy apparatus and a radiation irradiating method according to the present invention, fluctuation of a dose of a radiation irradiated to a sample can be reduced.

DESCRIPTION OF THE PREFERRED EMBODIMENTS

Figure 1:
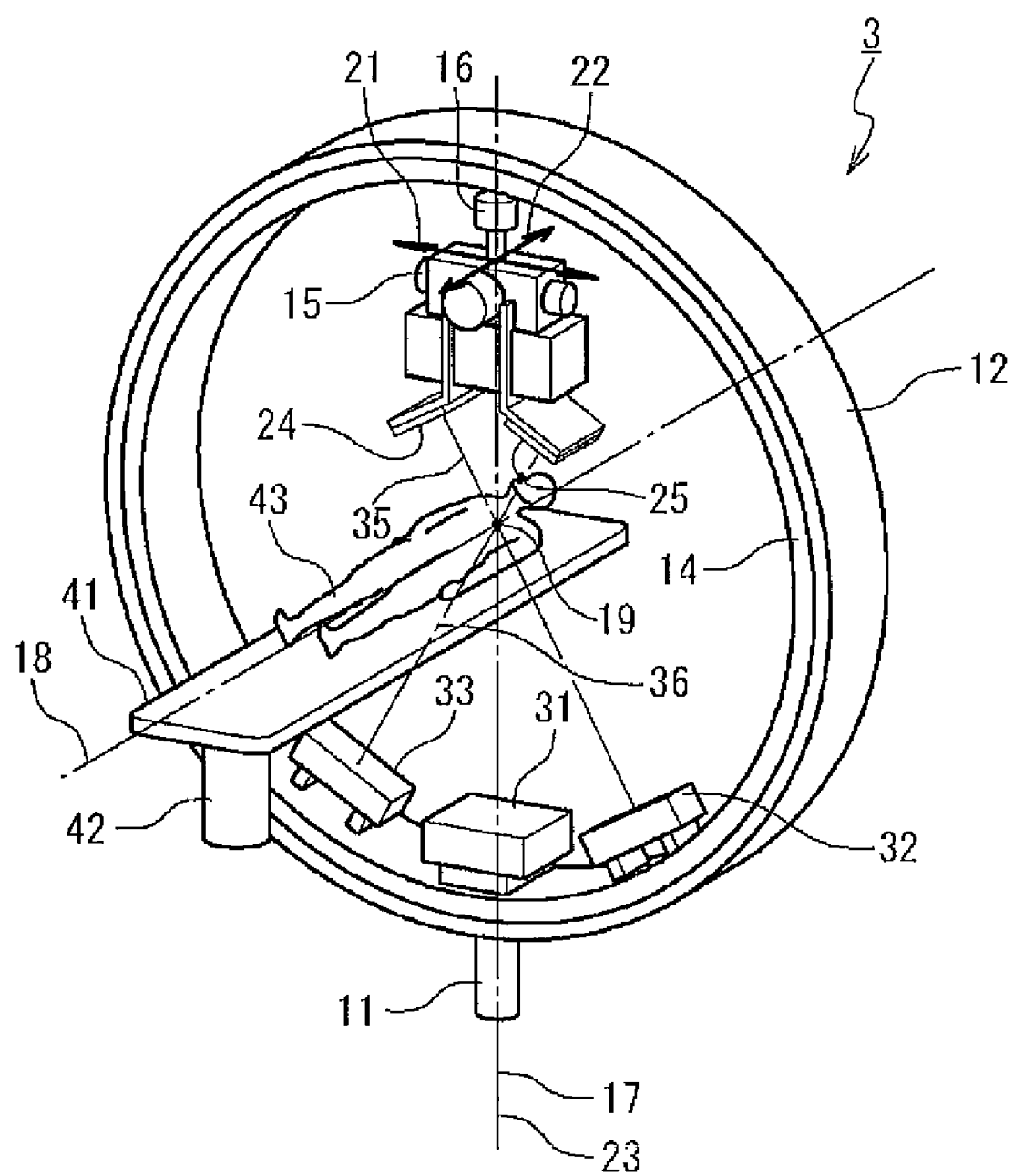
FIG. 1 is a perspective view showing a radiotherapy apparatus according to an embodiment of the present invention.

Hereinafter, a radiotherapy apparatus according to the present invention will be described with reference to the attached drawings. FIG. 1 is a diagram showing the radiotherapy apparatus 3 according to an embodiment of the present invention. As shown in FIG. 1, the radiotherapy apparatus 3 includes a rotation driving unit 11, an O-ring 12, a traveling gantry 14, a swinging mechanism 15, and an irradiating head 16. The rotation driving unit 11 supports the O-ring 12 on a base rotatably around a rotational axis 17, rotates the O-ring 12 around the rotational axis 17 under the control of a controller of the radiotherapy apparatus (not shown), and outputs a rotation angle of the O-ring 12 to the base. The rotational axis 17 is parallel to a vertical direction. The O-ring 12 is formed in a ring shape around a rotational axis 18, and supports the traveling gantry 14 rotatably around the rotational axis 18. The rotational axis 18 is perpendicular to the vertical direction, and extends through an isocenter 19 included in the rotational axis 17. The rotational axis 18 is further fixed to the O-ring 12, and, for this reason, rotates with the O-ring 12 around the rotational axis 17. The traveling gantry 14 is formed in a ring shape around the rotational axis 18, and is arranged concentrically to the ring of the O-ring 12. The radiotherapy apparatus 3 further includes a traveling drive unit (not shown). The traveling drive unit rotates the traveling gantry 14 around the rotational axis 18 under the control of the radiotherapy apparatus controller, and outputs a traveling angle of the traveling gantry 14 to the O-ring 12.

The swinging mechanism 15 is fixed inside the ring of the traveling gantry 14, and supports the irradiating head 16 on the traveling gantry 14 so that the irradiating head 16 can be arranged inside the traveling gantry 14. The swinging mechanism 15 has a pan axis 21 and a tilt axis 22. The pan axis 21 is fixed to the traveling gantry 14, and is parallel to the rotational axis 18 without intersecting with the rotational axis 18. The tilt axis 22 is orthogonal to the pan axis 21. The swinging mechanism 15 turns the irradiating head 16 around the pan axis 21 under the control of the radiotherapy apparatus controller, and turns the irradiating head 16 around the tilt axis 22.

The irradiating head 16 irradiates a therapeutic radiation 23 under the control of the radiotherapy apparatus controller. The therapeutic radiation 23 is irradiated almost along a straight line extending through an intersection at which the pan axis 21 and the tilt axis 22 intersect with each other. The therapeutic radiation 23 has a uniform distribution of intensity. Further, a shape of an irradiation field when the therapeutic radiation 23 is irradiated to a patient is controlled by shielding a part of the therapeutic radiation 23.

By supporting the irradiating head 16 by the traveling gantry 14 as described above and adjusting the irradiating head 16 by the swinging mechanism 15 once to face the isocenter 19, the therapeutic radiation 23 always passes through the isocenter 19 even when the O-ring 12 is rotated by the rotation driving unit 11 or the traveling gantry 14 is traveled by the traveling driving unit. That is, the therapeutic radiation 23 can be irradiated to the isocenter 19 from an arbitrary direction by the traveling and the rotating.

The radiotherapy apparatus 3 further includes a plurality of imager systems. That is, the radiotherapy apparatus 3 includes diagnostic X-ray sources 24 and 25 and sensor arrays 32 and 33. The diagnostic X-ray source 24 is supported by the traveling gantry 14. The diagnostic X-ray source 24 is provided inside the ring of the traveling gantry 14. The diagnostic X-ray source 24 is arranged at a position at which an angle between a line connecting the isocenter 19 and the diagnostic X-ray source 24 and a line connecting the isocenter 19 and the irradiating head 16 is an acute angle. The diagnostic X-ray source 24 irradiates a diagnostic X-ray 35 to the isocenter 19 under the control of the radiotherapy apparatus controller. The diagnostic X-ray 35 is a conical corn beam that is irradiated from one point included in the diagnostic X-ray source 24. The diagnostic X-ray source 25 is supported by the traveling gantry 14. The diagnostic X-ray source 25 is provided inside the ring of the traveling gantry 14, and is arranged at a position at which an angle between a line connecting the isocenter 19 and the diagnostic X-ray source 25 and the line connecting the isocenter 19 and the irradiating head 16 is an acute angle. The diagnostic X-ray source 25 irradiates a diagnostic X-ray 36 to the isocenter 19 under the control of the radiotherapy apparatus controller. The diagnostic X-ray 36 is a conical corn beam that is irradiated from one point included in the diagnostic X-ray source 25.

The sensor array 32 is supported by the traveling gantry 14. The sensor array 32 receives the diagnostic X-ray 35 that is irradiated by the diagnostic X-ray source 24 and transmits a target around the isocenter 19, and produces a transmission image of the target. The sensor array 33 is supported by the traveling gantry 14. The sensor array 33 receives the diagnostic X-ray 36 that is irradiated by the diagnostic X-ray source 25 and transmitted the target around the isocenter 19, and produces a transmission image of the target. As the sensor arrays 32 and 33, a FPD (Flat Panel Detector) and an X-ray II (Image Intensifier) are shown as examples.

According to these imager systems, transmission images around the isocenter 19 can be produced on the basis of image signals obtained by the sensor arrays 32 and 33.

The radiotherapy apparatus 3 further includes a sensor array 31. The sensor array 31 is arranged so that a line connecting the sensor array 31 and the therapeutic radiation irradiating head 16 passes through the isocenter 19, and is fixed inside the ring of the traveling gantry 14. The sensor array 31 receives the therapeutic radiation 23 that is irradiated by the irradiating head 16 and transmits the target around the isocenter 19, and produces a transmission image of the target. As the sensor array 31, the FPD (Flat Panel Detector) and the X-ray II (Image Intensifier) are shown as examples.

The radiotherapy apparatus 3 further include a couch 41 and a couch driving unit 42. A patient 43 to be treated by the radiotherapy apparatus 3 is laid on the couch 41. The couch 41 includes holding fixtures (not shown). The holding fixtures fix the patient to the couch 41 so that the patient cannot move. The couch driving unit 42 supports the couch 41 on the base, and moves the couch 41 under the control of the radiotherapy apparatus controller.

Figure 2:
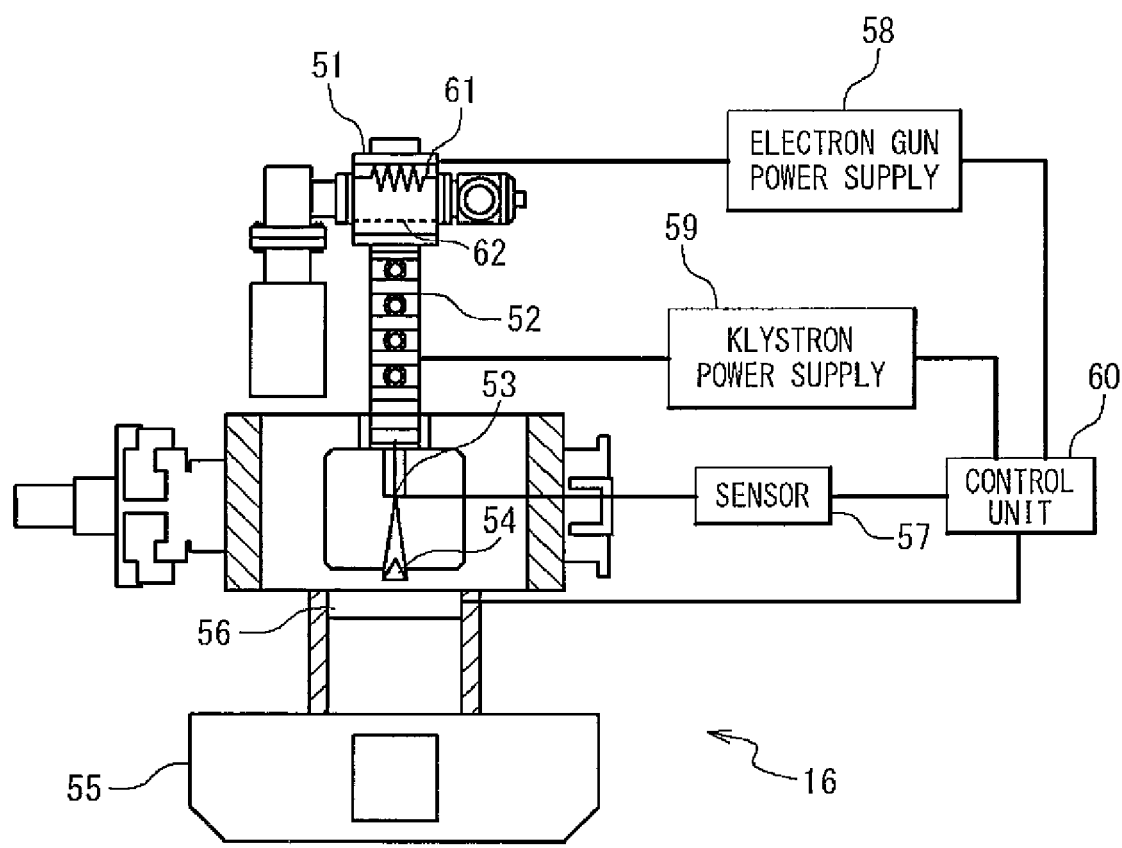
FIG. 2 is a diagram showing an irradiating head and other section in the radiotherapy apparatus of the embodiment.

FIG. 2 is a diagram showing the irradiating head 16. The irradiating head 16 includes an electron gun 51, an acceleration tube 52, an X-ray target 53, a flattening filter 54, and a multi-leaf collimator 55. The electron gun 51 includes a cathode 61 and a grid 62. The cathode 61 is heated by using a supplied electric power such that electrons can be easily emitted. The grid 62 is applied with a positive voltage so as for the electrons emitted from the cathode 61 to be led to the acceleration tube 52. The acceleration tube 52 accelerates the electrons emitted from the electron gun 51 by using supplied high-frequency power, to generate an electron beam and irradiates the electron beam to the X-ray target 53. The X-ray target 53 is formed of a material having higher atomic number. Tungsten, tungsten alloy, gold, and tantalum are exemplified as the material having the higher atomic number. The X-ray target 53 generates a radiation (X-ray) due to the bremsstrahlung effect caused when the electron beam generated by the acceleration tube 52 is irradiated. The radiation is irradiated almost along a straight line passing through a virtual point radiation source that is a point included internally in the X-ray target 53. The flattening filter 54 is formed of aluminum and the like, and is a plate having an approximately conical projection. The projection is arranged on an X-ray target 53 side. The flattening filter 54 is formed such that a dose of the radiation in a predetermined area of a plane perpendicular to its irradiation direction after the radiation irradiated from the X-ray target 53 passes the flattening filter 54 is almost uniformly distributed. The multi-leaf collimator 55 controls the shape of the irradiation field under the control of the radiotherapy apparatus controller such that a part of the therapeutic radiation 23 transmitted through the flattening filter 54 and then irradiated to the patient is shielded.

The radiotherapy apparatus 3 further includes a transmission type dosimeter 56, a sensor 57, an electric gun power supply 58, a klystron 59, and a control unit 60. The transmission type dosimeter 56, the sensor 57, the electric gun power supply 58, and the klystron 59 are connected to the control unit 60 to communicate with the control unit 60. The transmission type dosimeter 56 is arranged in such a manner that the radiation transmits the flattening filter 54 and then transmits the dosimeter 56. The transmission type dosimeter 56 includes a gas medium which can be ionized by the X-ray, electrodes between which a high voltage is applied, and a container including the gas medium and the electrodes thereinside. The transmission type dosimeter 56 measures a dose of the transmitted radiation on the basis of a current flowing between the electrodes, and outputs the measured dose to the control unit 60. The sensor 57 measures an electric current flowing through the X-ray target 53 when the electron beam generated by the acceleration tube 52 is irradiated to the X-ray target 53, and outputs the measured electric current to the control unit 60. The electric gun power supply 58 is connected to the electron gun 51. The electric gun power supply 58, supplies predetermined electric power to the cathode 61 of the electron gun 51 under the control of the control unit 60 and applies a predetermined voltage to the grid 62 of the electron gun 51. The klystron 59 is connected to the acceleration tube 52 via a wave guide tube. The klystron 59 supplies the high-frequency power to the acceleration tube 52 via the wave guide tube under the control of the control unit 60. The high-frequency power includes periodical pulses. The pulses of microwaves are formed. However, the klystron 59 can be replaced with another high-frequency power supply. A magnetron and a multi-electrode tube are exemplified as the high-frequency source.

The control unit 60 is a computer, and includes a CPU, a storage unit, an input unit, an output unit, and an interface (not shown). The CPU executes a computer program installed in the control unit 60, and controls the storage unit, the input unit, the output unit, and the interface. The storage unit stores the computer program and temporarily stores data produced by the CPU. The input unit produces data due to a user operation and outputs the produced data to the CPU. A keyboard is exemplified as the input unit. The output unit outputs data produced by the CPU so that the data can be recognized by the user. A display is exemplified as the output unit. The interface outputs data produced by external equipment connected with the control unit 60 to the CPU, and outputs data produced by the CPU to the external equipment. The external equipment includes the transmission type dosimeter 56, the sensor 57, the electron gun power supply 58, and the klystron 59.

Figure 3:
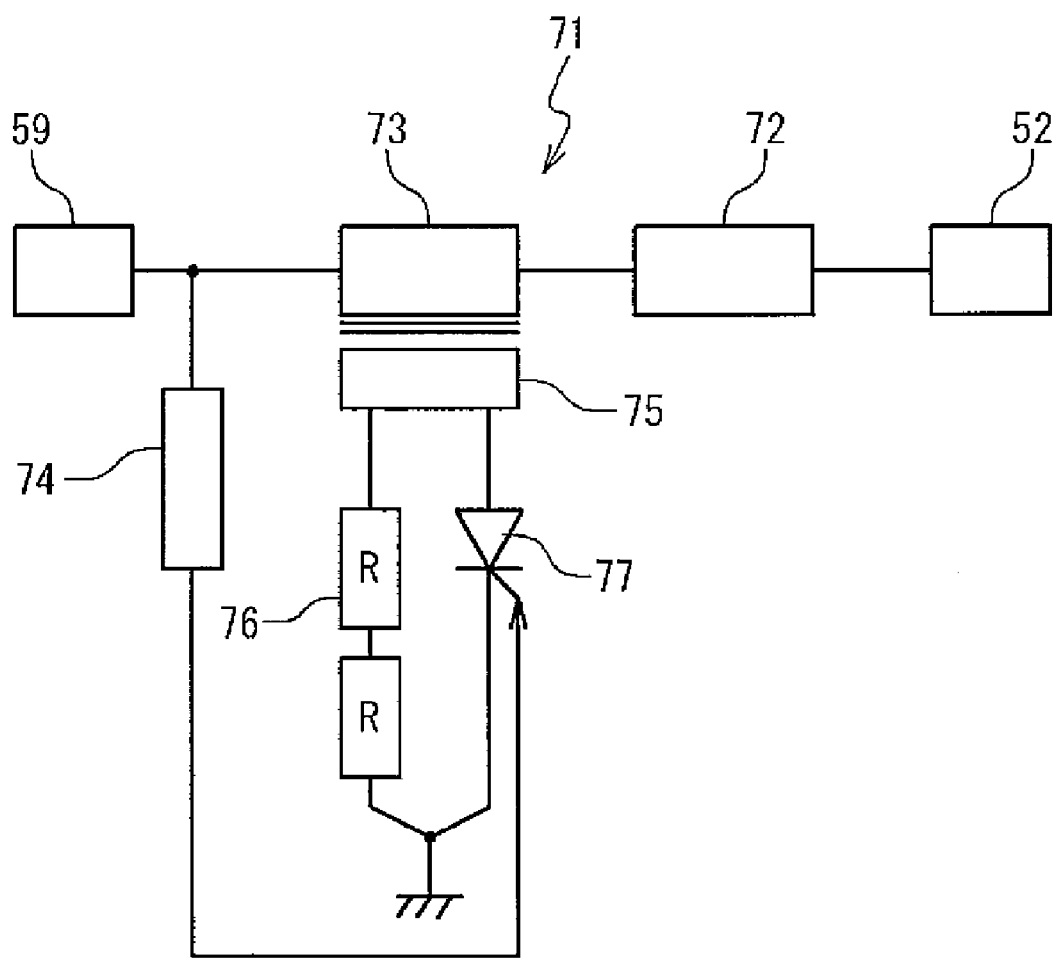
FIG. 3 is a circuit diagram showing a de-Qing circuit and a charging element in the radiotherapy apparatus of the embodiment.

As shown in FIG. 3, the radiotherapy apparatus 3 further includes a de-Qing circuit 71 and a charging element 72. The charging element 72 is provided in the course of the wave guide tube connecting the klystron 59 to the acceleration tube 52. The charging element 72 is formed from a capacitor. The de-Qing circuit 71 includes a charging choke coil 73, a voltage monitor 74, a secondary coil 75, a resistor 76, and a thyristor 77. The charging choke coil 73 is provided in the course of the wave guide tube between the klystron 59 and the charging element 72. The charging choke coil 73 is formed from an inductance element. The voltage monitor 74 measures a voltage of a node between the charging choke coil 73 and the de-Qing circuit 71, and outputs an electric signal when the measured voltage exceeds a predetermined voltage. The secondary coil 75, the resistor 76, and the thyristor 77 form a closed circuit. The secondary coil 75 is a secondary coil of the charging choke coil 73. The thyristor 77 forms the closed circuit when the voltage monitor 74 outputs the electric signal, and opens the circuit when the voltage monitor 74 does not output the electric signal. On this occasion, in the de-Qing circuit 71, the inductance of the charging choke coil 73 changes when a voltage of the high-frequency power supplied from the klystron 59 to the acceleration tube 52 exceeds a predetermined voltage, and thus the high-frequency power is prevented from being supplied to the acceleration tube 52.

According to the above described de-Qing circuit 71 and the charging element 72, the voltage of the high-frequency power supplied from the klystron 59 to the acceleration tube 52 is made constant. For this reason, a voltage in the acceleration tube 52 for accelerating electrons emitted by the electron gun 51 is controlled to be constant in an analog-like way, and energy applied by the acceleration tube 52 to the electrons emitted by the electron gun 51 becomes constant.

Figure 4:
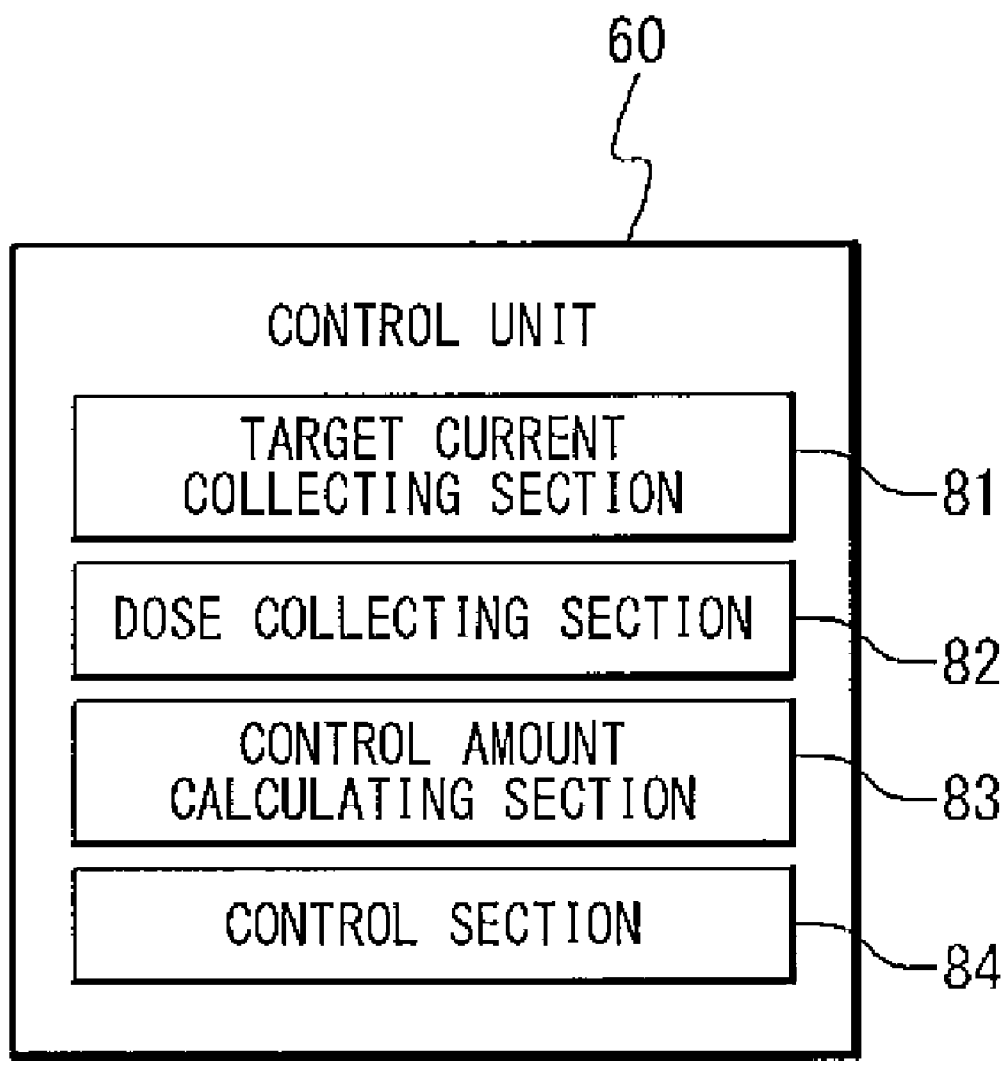
FIG. 4 is a block diagram showing a control unit in the radiotherapy apparatus of the embodiment.

As shown in FIG. 4, the computer program installed in the control unit 60 includes a target current collecting section 81, a dose collecting section 82, a control amount calculating section 83, and a control section 84. The target current collecting section 81 controls the sensor 57 to measures an electric current flowing through the target 53, and to output the measured current value. The dose collecting section 82 controls the transmission type dosimeter 56 to measure a dose of a radiation transmitted the transmission type dosimeter 56, and to output the measured dose. The control amount calculating section 83 calculates a control amount on the basis of the measured current value outputted from the target current collecting section 81 and the measured dose outputted from the dose collection part 82. The control amount shows a quotient calculated by dividing the measured electric current by the measured dose. The control section 84 controls the electric gun power supply 58 in a feedback manner so that the control amount calculated by the control amount calculating section 83 can become a predetermined constant value. That is, the control section 84 updates electric power supplied to the cathode 61 of the electron gun 51 by controlling the electric gun power supply 58 so that the control amount calculated by the control amount calculating section 83 can become a predetermined constant value.

A radiation irradiating method according to the embodiment of the present invention is carried out by using the radiotherapy apparatus 3. A user firstly creates a therapy plan. The therapy plan shows irradiation angles at which the therapeutic radiation 23 is irradiated to the affected region of the patient 43 and shows dose and property of the therapeutic radiation 23 irradiated from the respective irradiation angles. The user fixes the patient 43 to the couch 41 of the radiotherapy apparatus 3. The controller of the radiotherapy apparatus 3 adjusts positions of the irradiating head 16 and the patient 43 by using the rotation driving unit 11, the traveling drive unit, and the couch driving unit 42 so that the therapeutic radiation 23 can be irradiated to the patient 43 at the irradiation angles shown by the therapy plan.

Subsequently, the radiotherapy apparatus controller repeatedly performs a tracking operation and the irradiating operation. In the tracking operation, the radiotherapy apparatus controller calculates a position of the affected region on the basis of images taken by the imager system of the radiotherapy apparatus 3. The radiotherapy apparatus control unit drives, by using the swinging mechanism 15, the irradiating head 16 so that the therapeutic radiation 23 can be transmitted through the affected region. In the irradiating operation, the radiotherapy apparatus control unit 60 irradiates, by using the irradiating head 16, the therapeutic radiation 23 to the affected region immediately after the irradiating head 16 is moved by the tracking operation.

The control unit 60 collects the electric current flowing through the target 53 from the sensor 57 during the irradiating operation, and collects a dose of the radiation transmitted the transmission type dosimeter 56 from the transmission type dosimeter 56. The control unit 60 calculates the control amount based on the collected electric current and dose. The control amount shows a quotient calculated by dividing the collected electric current by the collected dose. The control unit 60 updates the electric power supplied to the cathode 61 of the electron gun 51 by controlling the electric gun power supply 58 in a feedback manner so that the calculated control amount can become a predetermined constant value.

It is known that a dose $R_{x\text{-}ray}$ of the X-ray emitted from the target 53 is proportional to a charge amount (electric current) $S_t$ per unit time in the electron beam colliding to the target 53 and that an energy distribution and generation-space distribution of the X-ray change depending on an energy distribution $E_{eb}$ of the colliding electron beam. That is, the following expression (1) is met:

$$R_{x\text{-}ray} = k_1 \times S_t \times f_t(E_{eb}) \qquad (1)$$

where $k_1$ is a constant, and the $f_t(E_{eb})$ is a function specific to the target 53 which shows a proportion of the X-ray generated when the electron beam having the energy distribution $E_{eb}$ collides to the target 53. It is known that a dose $S_d$ measured by the transmission type dosimeter 56 can be expressed by the following expression:

$$S_d = k_2 \times R_{x\text{-}ray} \times f_d(E_{x\text{-}ray}) \qquad (2),$$

where $k_2$ is a constant, the $E_{x\text{-}ray}$ is an X-ray energy distribution of the X-ray emitted from the target 53, and the $f_d(E_{x\text{-}ray})$ is a function specific to the transmission type dosimeter 56 which shows a proportion of ionization of the gas medium in the transmission type dosimeter 56 when the X-ray having the X-ray energy distribution $E_{x\text{-}ray}$ is irradiated to the transmission type dosimeter 56. The expressions (1) and (2) can be developed into the following expression:

$$f_t(E_{eb}) \times f_d(E_{x\text{-}ray}) = 1/(k_1 \times k_2) \times S_d/S_t \qquad (3)$$

It is known that an X-ray absorption dose "Dose" absorbed by the affected region of the patient 43 depends on the dose $S_d$ measured by the transmission type dosimeter 56 and the X-ray energy distribution $E_{x\text{-}ray}$, which is developed into the following expression:

$$\text{Dose} = k_3 \times S_d \times f(E_{x\text{-}ray}) \tag{4}$$

where $k_3$ is a constant, the $f(E_{x\text{-}ray})$ is a function specific to the patient 43 which shows a proportion of the X-ray absorbed by the patient 43 when the X-ray having the X-ray energy distribution $E_{x\text{-}ray}$ is irradiated to the patient 43.

The expressions (3) and (4) show that the X-ray absorption does "Dose" to the affected region of the patient 43 becomes constant when a quotient $S_d/S_t$ calculated by dividing the dose $S_d$ by the electric current $S_t$ is controlled to be constant and that the X-ray absorption dose of the therapeutic radiation 23 becomes constant, which is generated by the radiotherapy apparatus 3 and absorbed in the affected region of the patient 43. That is, when both of the electric current $S_t$ and the dose $S_d$ are constant, the X-ray absorption dose "Dose" is also constant, and when the quotient $S_d/S_t$ is constant, the X-ray absorption dose "Dose" even when each of the electric current $S_t$ and the dose $S_d$ changes. Consequently, the radiotherapy apparatus 3 can irradiate only a predetermined dose of the therapeutic radiation to the affected region of the patient 43 more accurately because the fluctuation of the X-ray absorption dose in the therapeutic radiation 23 absorbed by the patient 43 is small.

Figure 5:
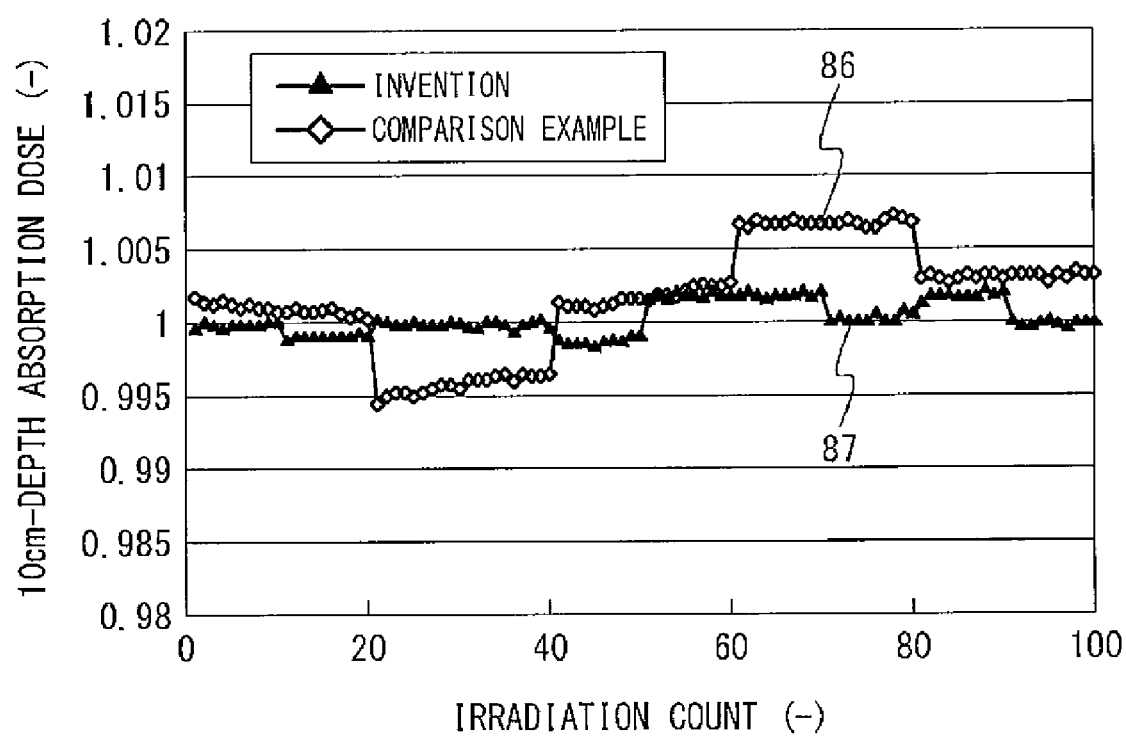
FIG. 5 is a graph showing fluctuation of a 10 cm-depth absorbed dose in a comparison example and fluctuation of a 10 cm-depth absorbed dose of a therapeutic radiation generated by the radiotherapy apparatus according to the present invention.

FIG. 5 shows a fluctuation of a 10 cm-depth absorbed dose of a therapeutic radiation generated by a comparison example of a radiotherapy apparatus according to the present invention. In the radiotherapy apparatus of the comparison example, the control unit 60 in the radiotherapy apparatus 3 according to the aforementioned embodiment is replaced by another controller. In the controller, a pulse width of a pulse of the high-frequency power generated by the klystron 59 is controlled so that a dose measured by the transmission type dosimeter 56 is constant. The 10 cm-depth absorption dose is generally equivalent to a dose of the X-ray absorbed in a human body, and a measuring method thereof is well known. The fluctuation 86 shows that a dose of the therapeutic radiation changes depending on a change of environment that the radiotherapy apparatus is provided and that dispersion (the standard deviation) of the 10 cm-depth absorbed dose of the therapeutic radiation is relatively high.

FIG. 5 further shows a fluctuation of the 10 cm-depth absorbed dose of the therapeutic radiation generated by the radiotherapy apparatus 3 according to the present invention. The fluctuation 87 shows that the dispersion of the 10 cm-depth absorbed dose is low compared to the fluctuation 86. That is, the fluctuation 87 shows that the radiotherapy apparatus 3 according to the present invention can irradiate only a predetermined dose of the therapeutic radiation to the affected region of the patient 43 more accurately, compared to the comparison example.

In another embodiment of the radiotherapy apparatus according to the present inventions the control section 84 of the control unit 60 according to the aforementioned embodiment is replaced by another control section. The control section controls the electron gun power supply 58 in the feedback manner so that the control amount calculated by the control amount calculating section 83 can be a predetermined constant value, and updates a voltage applied to the grid 62 of the electron gun 51. The above-described radiotherapy apparatus can reduce the fluctuation of the X-ray absorption dose of the therapeutic radiation 23 absorbed in the affected region of the patient 43 and can irradiate only a predetermined dose of the therapeutic radiation to the affected region more accurately in the same manner as that of the radiotherapy apparatus 3 according to the aforementioned embodiment. In addition, the control section controls the electron gun power supply 58 in the feedback manner so that the control amount calculated by the control amount calculating section 83 can be a predetermined constant value, and also can updates both of the electric power supplied to the cathode 61 of the electron gun 51 and the voltage applied to the grid 62. This radiotherapy apparatus can reduce the fluctuation of the X-ray absorption dose of the therapeutic radiation 23 absorbed in the affected region in the body of the patient 43 and can irradiate only a predetermined dose of the therapeutic radiation to the affected region more accurately in the same manner as that of the radiotherapy apparatus 3 according to the aforementioned embodiment.

In the radiotherapy apparatus according to another embodiment of the present invention, the control section 84 of the control unit 60 according to the aforementioned embodiment is replaced by another control section. The control section controls the klystron 59 in the feedback manner so that the control amount calculated by the control amount calculating section 83 can be a predetermined constant value, and updates a pulse width of a pulse of the high-frequency power supplied to the acceleration tube 52. The control section further controls the electron gun power supply 58 to supply constant electric power to the cathode 61 of the electron gun 51 and to apply a constant voltage to the grid 62 of the electron gun 51. This radiotherapy apparatus can reduce the fluctuation of the X-ray absorption dose of the therapeutic radiation 23 absorbed in the affected region in the body of the patient 43 and can irradiate only a predetermined dose of the therapeutic radiation to the affected region more accurately in the same manner as that of the radiotherapy apparatus 3 according to the aforementioned embodiment.

In addition, the control section also can control the electron gun power supply 58 in the feedback manner so that the electric current measured by the sensor 57 can be constant, and update the electric power supplied to the cathode 61 of the electron gun 51 or update the voltage applied to the grid 62 of the electron gun 51. Moreover, the radiotherapy apparatus further includes a sensor for measuring an electric current flowing between the cathode 61 and grid 62 of the electron gun 51. On this occasion, the control section can control the electron gun power supply 58 in the feedback manner so that the electric current measured by the sensor can be constant, and update the electric power supplied to the cathode 61 of the electron gun 51 or update the voltage applied to the grid 62 of the electron gun 51. Also, in this case, the radiotherapy apparatus can reduce the fluctuation of the X-ray absorption dose of the therapeutic radiation 23 absorbed in the affected region in the body of the patient 43 and can irradiate only a predetermined dose of the therapeutic radiation to the affected region more accurately in the same manner as that of the radiotherapy apparatus 3 according to the aforementioned embodiment.

What is claimed is:

1. A radiotherapy apparatus comprising:
    an acceleration unit configured to generate a charged particle beam;
    a target configured to generate x-ray radiation when the charged particle beam is irradiated to said target;
    a sensor configured to measure an electric current flowing through said target;
    a dosimeter configured to measure a dose of the x-ray radiation; and a control unit configured to control said acceleration unit based on the measured electric current and the measured dose, wherein said control unit controls said acceleration unit based on a quotient obtained when the measured dose or a dose per a predetermined time is divided by the measured electric current.

2. The radiotherapy apparatus according to claim 1, wherein said control unit performs a feedback control on said acceleration unit such that the quotient is constant.

3. The radiotherapy apparatus according to claim 2, wherein said acceleration unit comprises:

an electron gun configured to emit charged particles;

an accelerating tube power supply configured to generate high frequency power;

an accelerating tube configured to accelerate the charged particles by using the high frequency power to generate the charged particle beam, said control unit controls said accelerating tube power supply such that the quotient is constant.

4. The radiotherapy apparatus according to claim 3, wherein said acceleration unit further comprises:

an electron gun power supply configured to generate charged particle emission power, said electron gun emits the charged particles by using the charged particle emission power, and said control unit controls said electron gun power supply such that an emission amount of the charged particles is constant.

5. The radiotherapy apparatus according to claim 2, wherein said acceleration unit comprises:

an electric gun power supply configured to generate charged particle emission power;

an electron gun configured to emit charged particles by using the charged particle emission power; and an accelerating tube configured to accelerate the charged particles to generate the charged particle beam, wherein said control unit controls said electric gun power supply such that the quotient is constant.

6. The radiotherapy apparatus according to claim 5, wherein said electron gun power supply has a function to generate cathode heat power, and said electron gun comprises a cathode configured to emit the charged particles by the cathode heat power.

7. The radiotherapy apparatus according to claim 5, wherein said electron gun power supply has a function to generate a grid voltage, and said electron gun comprises:

a cathode configured to emit the charged particles; and a grid configured to accelerate the charged particles by using the grid voltage.

8. The radiotherapy apparatus according to claim 2, wherein said acceleration unit further comprises an accelerating tube power supply configured to generate high frequency power, said accelerating tube accelerates the charged particles by using the high frequency power to generate the charged particle beam, and said control unit controls said accelerating tube power supply such that the high frequency power is constant.

9. The radiotherapy apparatus according to claim 8, wherein said accelerating tube power supply comprises a de-Qing circuit configured to makes a voltage of the high frequency power constant.

10. A radiation irradiating method comprising:

measuring electric current flowing through a target which irradiates x-ray radiation when a charged particle beam generated by an acceleration unit is irradiated;

measuring a dose of the x-ray radiation; and controlling said acceleration unit based on the measured electric current and the measured dose, wherein said controlling comprises:

controlling said acceleration unit based on a quotient obtained when the measured dose or a dose per a predetermined time is divided by the measured electric current.

11. The radiation irradiating method according to claim 10, wherein said controlling comprises:

performing a feedback control on said acceleration unit such that the quotient is constant.

12. The radiation irradiating method according to claim 11, further comprising:

emitting charged particles from an electric gun;

generating high frequency power by an accelerating tube power supply; and accelerating the charged particles by using the high frequency power to generate the charged particle beam, wherein said controlling comprises:

controlling said accelerating tube power supply such that the quotient is constant.

13. The radiation irradiating method according to claim 12, further comprising:

generating charged particle emission power by an electron gun power supply, wherein said emitting comprises:

emitting the charged particles by using the charged particle emission power, and said controlling comprises:

controlling said electron gun power supply such that an emission amount of the charged particles is constant.

14. The radiation irradiating method according to claim 11, further comprising:

generating charged particle emission power from an electric gun power supply;

emitting the charged particles by using the charged particle emission power; and accelerating the charged particles to generate the charged particle beam, wherein said controlling comprises:

controlling said electric gun power supply such that the quotient is constant.

15. The radiation irradiating method according to claim 14, further comprising:

generating high frequency power from an accelerating tube power supply, wherein said accelerating the charged particles comprises:

accelerating the charged particles by using the high frequency power to generate the charged particle beam, and said controlling comprises:

controlling said accelerating tube power supply such that the high frequency power is constant.

16. The radiation irradiating method according to claim 14, wherein said emitting comprises:

generating cathode heat power from said electron gun power supply; and emitting the charged particles from a cathode of said electric gun with the cathode heat power.

17. The radiation irradiating method according to claim 14, wherein said accelerating the charged particles comprises:

generating a grid voltage; and accelerating the charged particles by using the grid voltage.

* * * * *